United States Patent
Su et al.

(10) Patent No.: US 7,128,755 B2
(45) Date of Patent: Oct. 31, 2006

(54) EXPANDABLE BIODEGRADABLE POLYMERIC STENTS FOR COMBINED MECHANICAL SUPPORT AND PHARMACOLOGICAL OR RADIATION THERAPY

(75) Inventors: Shih-Horng Su, Westford, MA (US); Robert C. Eberhart, Dallas, TX (US)

(73) Assignee: Texas Stent Technologies, Inc., Dallas, TX (US)

( * ) Notice: Subject to any disclaimer, the term of this patent is extended or adjusted under 35 U.S.C. 154(b) by 462 days.

(21) Appl. No.: 10/143,676

(22) Filed: May 10, 2002

(65) Prior Publication Data
US 2002/0183830 A1    Dec. 5, 2002

Related U.S. Application Data

(60) Provisional application No. 60/295,039, filed on Jun. 1, 2001.

(51) Int. Cl.
*A61F 2/06*  (2006.01)
(52) U.S. Cl. .................. 623/1.15; 623/1.22; 623/1.38; 623/1.42
(58) Field of Classification Search ............... 623/1.15, 623/1.22
See application file for complete search history.

(56) References Cited

U.S. PATENT DOCUMENTS

| | | | |
|---|---|---|---|
| 5,591,222 A | | 1/1997 | Susawa et al. |
| 5,609,629 A | * | 3/1997 | Fearnot et al. ............. 623/1.42 |
| 5,733,327 A | | 3/1998 | Igaki et al. |
| 6,045,568 A | | 4/2000 | Igaki et al. |
| 6,080,177 A | | 6/2000 | Igaki et al. |
| 6,171,338 B1 | * | 1/2001 | Talja et al. ................ 623/1.22 |
| 6,368,346 B1 | | 4/2002 | Jadhav |
| 6,379,380 B1 | | 4/2002 | Satz |
| 6,379,382 B1 | | 4/2002 | Yang |
| 6,497,724 B1 | * | 12/2002 | Stevens et al. ............ 623/1.22 |

OTHER PUBLICATIONS http://www.turmeric-curcumin.com/main.html.*
Circulation, vol. 102, pp. 399-404, Feb. 15, 2000.

* cited by examiner

*Primary Examiner*—Julian W. Woo
*Assistant Examiner*—Sarah Webb
(74) *Attorney, Agent, or Firm*—Fish & Richardson P.C.

(57) ABSTRACT

An expandable biodegradable polymeric stent is fabricated with biodegradable polymer fibers (Poly-L-lactic acid, PLLA) in a coil shape that is constructed with both central and external or internal peripheral lobes. It is delivered and expanded using a conventional angioplasty balloon system. The disclosed stent can serve as a temporary scaffold for coronary vessels after PTCA or for peripheral endovascular stenting, or it can provide mechanical palliation for strictures of ductile organs (trachea, esophagus, bile and pancreatic ducts, ureter etc.). The disclosed stent also serves as a unique device for specific local drug delivery. Therapeutic agents (chemical compounds, protein enzyme and DNA sequences) and cells can be loaded into the stent and gradually released to target tissues. Local radiation therapy can also be delivered by a specially adapted stent.

19 Claims, 2 Drawing Sheets

EXPANDABLE BIODEGRADABLE POLYMERIC STENTS FOR COMBINED MECHANICAL SUPPORT AND PHARMACOLOGICAL OR RADIATION THERAPY

This application claims priority from provisional application Ser. No. 60/295,039, filed Jun. 1, 2001.

TECHNICAL FIELD OF THE INVENTION

This invention generally relates to stents for implantation into blood vessels or other organs, and more specifically to stents that are absorbable over time and capable of local drag/gene delivery for enhancing therapeutic effects.

BACKGROUND OF THE INVENTION

Intraluminal stents are commonly employed for treatment of various vascular conditions such as arteriosclerosis, often as coronary artery implants. A stent can be implanted at the site of a vessel stricture or steno sis using a conventional balloon catheter delivery system as used in angioplasty. Stents also maybe employed in body passageways other than blood vessels to treat strictures or prevent luminal occlusion. Such stents ordinarily consist of a cylindrical network of very small metal wires. The stent is inserted in a small-diameter configuration and then expanded to a large-diameter final configuration against the walls of the blood vessel or other body lumen. Such stent structures and implantation techniques are well known.

Great efforts have been expended to modify metallic stents to eliminate stress-induced and/or inflammation-induced restenosis, and to effectively deliver therapeutic agents to lesion sites. Some advancements in drug-coated metal stents have been made recently. However, metallic stents still present a potential vessel injury problem. Furthermore, the delivery of medicine to a lesion site either by local or systemic means is unsatisfactory with current stent and catheter technology. The present invention addresses these problems.

SUMMARY OF THE INVENTION

In accordance with a principal object of the present invention, luminal support and localized treatment of lesion sites within body passageways is accomplished by the implantation of an expandable biodegradable polymeric stent that includes therapeutic agents. By virtue of its gradual absorption over time, the inventive stent avoids residual stress, and permits local drug delivery or local radiation treatment.

In its preferred implantation, the stent of the present invention provides adequate mechanical support during and following the interventional procedure, and, by being absorbed over controllable periods, avoids chronic mechanical disturbance of the vessel wall. The residual stress against the vessel wall is eliminated after the stent is degraded. During the degradation process, loaded therapeutic agents are released in a controlled fashion, and effective concentrations at target lesions can be maintained. Local radiation treatment can likewise be maintained.

The stent of the present invention preferably has the following features: (1) it has an all-polymer construction with similar mechanical function to conventional metallic stents; (2) it is constructed with fiber cords having both central and peripheral lobes and is stabilized by longitudinal rods, thus presenting a low profile during delivery and a large effective diameter following expansion; (3) it is expandable with an expansion ratio that can be customized to meet various needs; (4) it can be deployed at body temperature with low inflation pressure (3 atm); (5) it is a temporary implant; (6) it may be a local drug or gene delivery device; (7) it may be a local radiation therapy device; and (8) it can include fibers with various functions (mechanical support, acute drug burst, long-term drug release, etc.), enabling a variety of treatment options including multiple functions with a single stent and using a single stent-implant procedure.

The present invention has a number of advantages over conventional stents. Firstly, in contrast to metal stents, the polymeric stent of the present invention is a temporary implant. The temporary residence permits the residual stress against the vessel wall to be resolved, a factor commonly leading to in-stent restenosis in the case of metallic stents. Secondly, the inventive stent is also capable of carrying therapeutic agents either incorporated in the polymer bulk or coated on the polymer surface. Thirdly, it is possible to control the operation of the inventive stent by selection of the polymer composition, the polymer molecular weight, fiber cord diameter and processing conditions, thus controlling the degradation rate, drug release rate and period of mechanical support. Fourthly, compared with tubular-shaped polymeric stents, the inventive stent has superior expandability and flexibility. Additionally, the inventive stent also has advantages over the "zigzag" polymeric stent recently disclosed in the prior art (*Circulation,* vol. 102, pp. 399–404, 2000), since it is deployed at body temperature with low inflation pressure.

In addition to being biodegradable, the stent of the present invention synergistically combines excellent mechanical support and local drug delivery, for both short-term and long-term applications. Current metallic stents are incapable of delivering drugs without polymer coatings. Moreover, metallic stents are known to be a stimulus for chronic vessel injury. Other current approaches, such as the combination of a metallic stent and bolus drug delivery by a porous angioplasty balloon, provide both mechanical support and short-term drug delivery. However, other than initial control of drug concentration at the lesion site, the porous angioplasty balloon approach is limited in its application and is incapable of performing certain desirable functions, such as prolonged drug delivery and transient radiation therapy. The biodegradable polymeric stent of the present invention provides sufficient mechanical strength as well as controllable short-term and long-term drug delivery while eliminating the stimulus for chronic vessel wall injury.

BRIEF DESCRIPTION OF THE DRAWINGS

For a more complete understanding of the present invention and the advantages thereof reference is now made to the following description taken in conjunction with the accompanying Drawings in which.

DETAILED DESCRIPTION OF THE INVENTION

Figure 1:
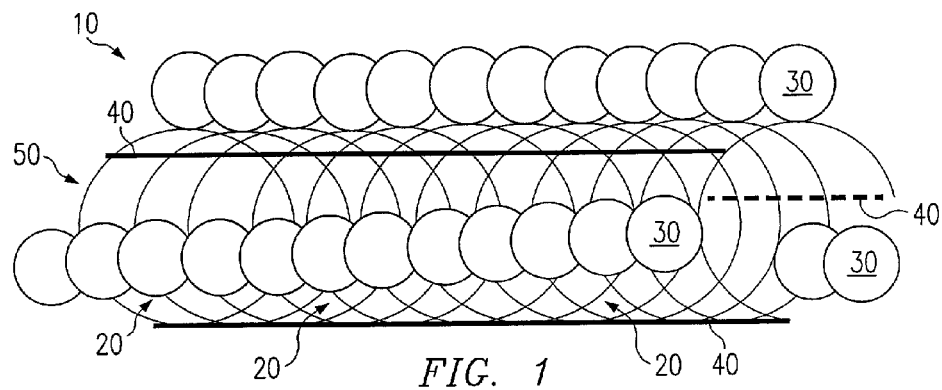
FIG. 1 is a schematic illustration of the three-dimensional structure of an expandable stent according to the present invention.

Referring to FIG. 1, a preferred embodiment of a stent according to the present invention is shown and generally designated by reference numeral 10. The stent 10 comprises a coiled cord 50 of non-metallic material, preferably a polymer fiber or ply of multiple polymer fibers, wherein the polymer preferably comprises Poly-L-Lactic Acid ("PLLA"). The use of PLLA to construct the stent 10 is advantageous because it is biodegradable. It degrades away gradually within the body, the chemical products of the degradation process being primarily carbon dioxide and water, which are harmless to the host patient. Degradation occurs over a period of about six months to three years, mainly depending on the molecular weight of the polymer employed. PLLA is also advantageous because it can be impregnated with drugs or other chemical agents for local treatment of tissue at the stent implant site.

Byway of example, the stent 10 of FIG. 1 is constructed with twelve coil rotations of a single-fiber cord, each rotation having one central lobe 20 and three peripheral lobes 30. The twelve central lobes 20 form the backbone of the stent 10. Three longitudinal rods 40 are attached on the exterior surface of the central lobes 20, preferably using a viscous PLLA-chloroform solution. The rods 40 may comprise the same single-fiber material as the coil of lobes 20 and 30. Alternatively, the coil of lobes 20 and 30 and the rods 40 may comprise a multiple-fiber ply material. For example, the coil of lobes 20 and 30 may be formed from a double-fiber ply material, and each of the three rods 40 may be formed from a triple-fiber ply material for added rigidity. Also, by way of example, the length of inventive stent is 15 mm and the initial diameter is 1.9 mm. In this example, the final diameter, after balloon expansion, can reach 3.24 mm. The length of the stent can be increased by increasing the number of coil rotations. The peripheral and central lobe diameters determine the final diameter of the stent. To assure mechanical integrity, it is preferred that the coiled lobes 20 and 30 of the stent 10 be formed from a single cord that is continuous end-to-end.

The mechanical strength of the stent 10 can easily be varied (1) by adjusting the coil density; or (2) by adjusting the fiber ply. In practice, a stent with 15 coil rotations and a length of 15 mm will be stronger than a stent of the same length with 12 rotations. However, a stent in which the cord 50 is composed of a multiple-fiber ply will have higher resistance to radial compression. A double-fiber ply will have about twice the radial compression resistance of a single-fiber construction, and triple-fiber ply will have about three times the radial compression resistance of a single-fiber construction. Additionally, the diameter of the stent 10 can be adjusted (1) by adjusting the diameter of central and peripheral lobes; or (2) by adjusting the number of multiple peripheral lobes per central lobe. The stent diameter increases as the diameter of central and peripheral lobes increases, and vise versa. It will also be appreciated that more peripheral lobes with the same diameter results in a stent of larger diameter in its fully expanded state.

The above-described design provides an excellent way to maximize the expandability of a polymeric stent. The major difference between metal and polymeric stent materials is that metal is more malleable and generally has a greater tensile strength. Thus, a metal wire can be deformed without affecting mechanical strength. In contrast, a polymer fiber cord cannot retain its original mechanical strength following permanent deformation (bending, for example). Despite the lower mechanical strength of polymeric materials relative to metals, the polymeric stent of the present invention has sufficient strength to retain its shape in the expanded state, thereby stabilizing the vessel or duct wall for the intended purposes as with a conventional metal stent.

In accordance with an important concept of the invention, an extra length of cord is provided by the peripheral lobes to facilitate expansion from the furled state to the final large-diameter state. If the desired final length of the stent in the furled, multiple-lobe configuration is known, stents can be prepared using the exact same initial length of cord. After expansion, the final deployed length is achieved without damaging cord. It will be appreciated that this approach to stent design and fabrication provides a polymeric stent with excellent mechanical strength and flexibility for effective implantation.

According to another important feature of the invention, the longitudinal rods 40 provide support for the flexible coiled cord 50. Furthermore, the longitudinal rods 40 maintain the axial length of the stent 10 constant as its radial dimension increases during expansion. Solid wall tubular stents have the practical limitations that they are relatively inflexible, making it difficult for them to pass through sometimes tortuous vessel networks. This is because their relatively rigid cylindrical structure reduces the freedom to bend in all directions. In this invention, the integrity of the stent 10 is maintained by the longitudinal rods 40, three in embodiment of FIG. 1 preferably arranged at 120° intervals. Therefore, the expandable stent 10 has the inherent flexibility of a coil design yet has sufficient rigidity for effective handling due to the presence of the longitudinal rods 40. The advantages of this design compared with currently available clinical metal models will be readily apparent to the skilled practitioner.

It should be mentioned that the number of longitudinal reinforcing rods can be selected based on the number of peripheral lobes that design considerations dictate. Preferably, the longitudinally aligned groups of peripheral lobes are equal in number to the longitudinal reinforcing rods, which are alternately positioned so that each rod is midway between its two neighboring peripheral lobe groups. In FIG. 1, the preferred arrangement is illustrated in which there are three longitudinal reinforcing rods 40 and three longitudinally aligned groups of peripheral lobes 30.

Prototypes of the inventive stent have been constructed using a fixture and manually winding a fiber cord in a spiral fashion along the fixture. The fixture employed included a central cylindrical mandrel attached to a base at one end, and three cylindrical side posts attached to the base and extending along and parallel to the mandrel, the posts being circumferentially spaced around the mandrel at 120° intervals. The stent is constructed by attaching one end of the cord to the free end of the mandrel, then winding the cord around the mandrel, and successively looping the cord around the posts moving downward toward the base until twelve rotations of the mandrel have been completed. Periodically during the winding process, each of three longitudinal rods 40 are attached to the central lobes 20 in the manner depicted in FIG. 1. Upon completion, the stent is slidably removed from the mandrel and side posts. Design of an automated system is contemplated for reducing the labor-intensive winding process used to make the prototype stents.

The stent delivery and deployment system is based on conventional balloon catheter delivery systems used currently in clinical angioplasty. Therefore, the stent of the present invention can be implanted in practice using much of the conventional clinical deployment techniques used with metal stents.

Figure 2A:
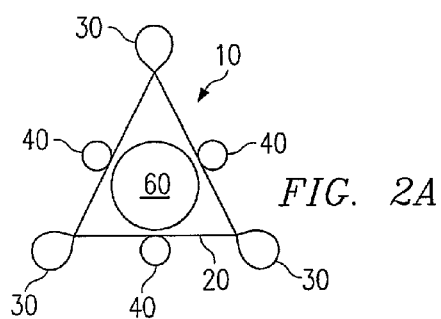
FIGS. 2A, 2B and 2C are schematic end views of the inventive stent at three stages during deployment with an inflatable balloon shown therein in phantom, FIG. 2A showing the stent in its furled state, FIG. 2B showing the stent in a partially expanded state, and FIG. 2C showing the stent in its fully expanded state.

FIGS. 2A–D illustrate the procedure of stent expansion and the structure of an expanded stent. In FIG. 2A, the stent 10 is in its small-diameter furled state, which enables the stent 10 to readily travel through a vessel to a site where it is to be deployed. A balloon 60, shown in phantom, is provided inside the stent 10 to effect expansion. In this end view, the symmetrical spacing of the three rods 40 with the three longitudinally aligned groups of peripheral lobes 30 can be envisioned more clearly when considered together with FIG. 1. In the small-diameter furled state, it will be seen that the central lobes 20 viewed from the end of the stent 10 are generally triangular in shape. Thus, the term "small-diameter" is used herein to describe the relative size of the stent 10 in the original furled state, the "diameter" this context being the effective diameter of a circle or imaginary cylinder tangentially contacting the outer ends of the peripheral lobes 30.

Figure 2B:
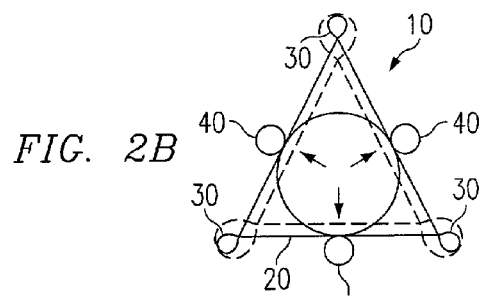

In FIG. 2B, the stent 10 is starting to expand under the force of the expanding balloon 60, as indicated by the arrows. For comparison, dashed lines are provided in FIG. 2B to show the configuration of the stent 10 in its original furled state as depicted in FIG. 2A.

Figure 2C:
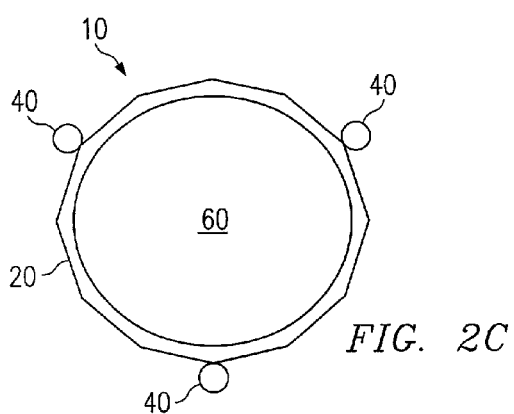

In FIG. 2C, the stent 10 is shown in its large-diameter, fully expanded state, in which the peripheral lobes 30 (shown in FIGS. 2A and 2B) have disappeared, their cord lengths having merged into the central lobe 20 of each of the twelve coils. Experimental data reveals that the stent 10 expands uniformly under increasing balloon pressure until it reaches its final diameter. The terms "final diameter" and "large-diameter" are used to describe the relative size of the stent 10 in its fully expanded state as depicted in FIG. 2C, the "diameter" being the effective diameter of a circle or imaginary cylinder tangentially contacting the outer edges of the longitudinal rods 40. FIG. 2C is not drawn to an accurate relative scale compared to FIG. 2A. In practice, it has been found that sufficient cord length can be provided in the peripheral lobes 30 to cause the effective diameter of the stent 10 to approximately double in size going from the original furled state of FIG. 2A to the final fully expanded state of FIG. 2C.

Figure 2D:
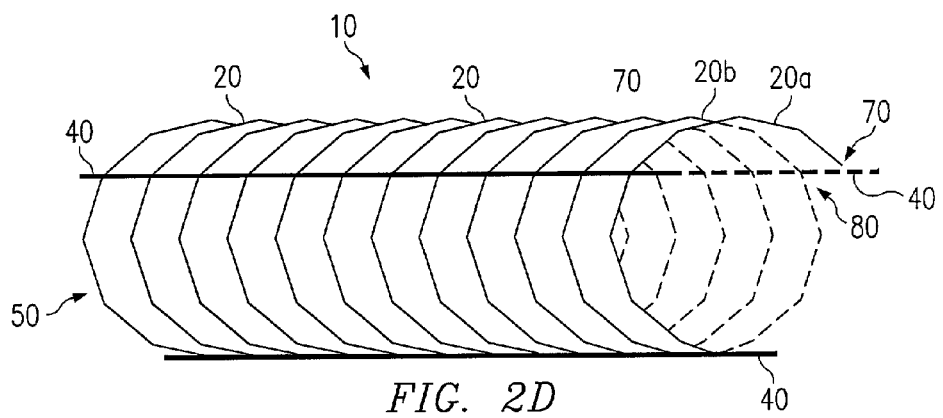
FIG. 2D is a schematic perspective view of the inventive stent in its fully expanded state.

FIG. 2D shows the stent 10 with the balloon removed in its large-diameter state and also depicts the longitudinal rods 40 in their 120° spaced peripheral positions along the length of the stent 10. The helical nature of the stent 10 in its fully expanded state is evident in FIG. 2D. Though the central lobes 20 are derived from a single cord of polymeric material that generally defines a helix in the fully expanded state, each lobe 20 can be viewed as one 360° length of cord with a leading end and a trailing end spaced apart by one-twelfth (in the case of a twelve-lobe stent) of the length of the stent 10. For example, to illustrate this concept, the first lobe 20a at the right end of the stent 10 of FIG. 2D has a leading end 70 and a trailing end 80. The trailing end 80 of the first lobe 20a corresponds to the leading end of the second lobe 20b. The pattern continues through the length of the stent 10, each lobe's trailing end corresponding to the next successive lobe's leading end until the last lobe is reached, whose trailing end (not shown in FIG. 2D) is the free end of the cord 50 at the left end of the stent 10.

It will be appreciated from FIGS. 1 and 2A that the stent 10 in its original furled state has a more complex shape. From the example shown in FIG. 2A, it will be appreciated that each central lobe 20 has three peripheral lobes 30, a leading one of which being defined by a portion of the cord 50 that adjoins the leading end of the corresponding central lobe 20, a trailing one of which being defined by a portion of the cord 50 that adjoins the trailing end of the corresponding central lobe 20, and the last of the three peripheral lobes 30 being defined by a portion of the cord 50 at an intermediate point of the corresponding central lobe 20.

The stent 10 of the present invention can be adapted to a broad range of inflation pressures from 3 to 10 atm (a maximum pressure possibly even exceeding 10 atm). Experimental data has shown that, using a double-fiber ply stent, full expansion occurs at about 3 atm, and that the fully expanded diameter is stably maintained at inflation pressures of up to 10 atm. In the above-described example, the stent 10 has limited recoil about 4% when in an unstressed condition. The collapsing pressure holds at least up to 16 psi (i.e., greater than 1 atm), which is comparable to conventional metal stents.

It will be appreciated that the preferred PLLA fibers preferably used for the stent fabrication can be loaded with a non-steroid type anti-inflammation agent, such as curcumin. The curcumin-loaded fibers significantly reduce inflammation at the stent implant site by reducing the adhesion of inflammatory cells. Other drugs can be used with the expandable biodegradable polymer stent of the present invention. The impregnated drugs can be prepared in a way that controllably delivers the drug over a predetermined time period.

Figure 3A:
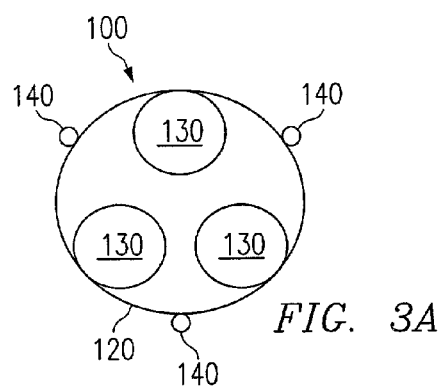
FIGS. 3A and 3B are schematic end views of an alternative embodiment of the inventive stent.
Figure 3B:
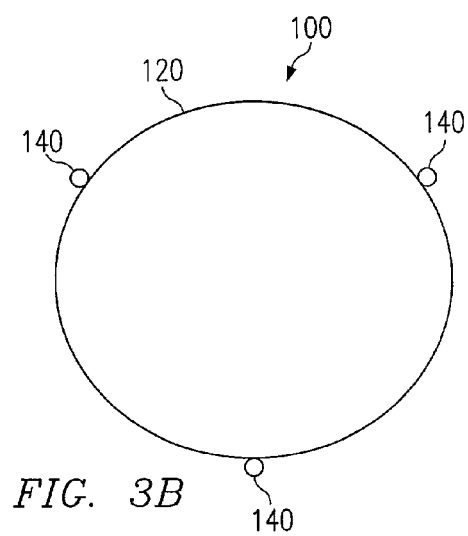

FIGS. 3A and 3B show an alternate embodiment of the inventive stent, generally designated by reference numeral 100. The stent 100 has a furled state shown in FIG. 3A in which the fiber coils are tightly furled and central lobes 120 (one shown) are confined to a small diameter. There are three peripheral lobes per coil, which are designated by numerals 130 and, in this embodiment, are located inside the central lobes 120. As in the previously-described embodiment of the stent 10 shown in FIG. 1, there may be twelve coils, which are formed from a continuous cord and extend longitudinally to define the body of the stent 100. Each coil has a large central lobe 120 and three internally-disposed peripheral lobes 130, shown in FIG. 3A. As in the previously described stent 10, the stent 100 has longitudinally extending rods 140 that support the coil structure. When the stent 100 is expanded as shown in FIG. 3B, the peripheral lobes merge into a single large-diameter central lobe 120 for each of the twelve coils of the stent 100. Using this construction of internal peripheral lobes 130, the ratio of the final expanded stent diameter to the initial furled stent diameter can be greater than a factor of two.

Those skilled in the art will appreciate that the inventive stent, in its disclosed embodiments or variations thereof, provides mechanical and therapeutic advantages over conventional stents. In addition, advantageous treatments will suggest themselves to the skilled practitioner considering the foregoing description of the invention. By virtue of the biodegradable polymeric nature of the inventive stent, the same vessel site can be retreated at a later time if needed, including staging procedures during growth of the patient. Similarly, successive treatments of a tissue that is changing size can be facilitated with the disclosed stent. It should also be noted that the inventive stent can be implanted at a site of healthy tissue for diagnostic purposes or therapeutic treatment of adjacent tissue.

Although preferred embodiments have been described and illustrated, it should be understood that various changes, substitutions and alterations can be made therein without departing from the spirit and scope of the invention as defined by the appended claims.

What is claimed is:

1. A non-metallic stent having a furled small-diameter state and an expanded large-diameter state, comprising, in the furled small-diameter state,
   a plurality of central lobes of approximately the same size arranged in succession at spaced intervals about a central core longitudinally defining a stent axis through said central core, and each said central lobe having at least a single central lobe bounding cord member segment about the periphery thereof, there being a leading end and a trailing end for each said at least single central lobe bounding cord member, the trailing end of each said at least single central lobe bounding cord member, other than the last in the succession, being interfaced to the leading end of the next successive said at least single central lobe bounding cord member;
   a plurality of peripheral lobes for providing the interface between the leading and trailing ends of said at least single central lobe bounding cord members, each said peripheral lobe having a peripheral lobe bounding cord member segment about the periphery thereof, with each said peripheral lobe bounding cord member segment having a leading end connected to the trailing end of one of said at least single central lobe bounding cord member segments and a trailing end connected to the leading end of one of said at least single central lobe bounding cord member segments so as to adjoin each central lobe; and
   a plurality of longitudinal rods attached to the sides of said at least single central lobe bounding cord members of said central lobes at multiple points around the periphery of the stent; and,
   comprising, in the expanded large-diameter state, the peripheral lobes merge into the central lobes.

2. The stent of claim 1, wherein said at least single central lobe bounding cord members of said central lobes and said peripheral lobe bounding cord members of said peripheral lobes are elements of a continuous polymeric fiber cord.

3. The stent of claim 2 wherein the polymeric fiber cord has a single-fiber construction.

4. The stent of claim 2 wherein the polymeric fiber cord has a multiple-fiber ply construction.

5. The stent of claim 2, wherein the polymeric material of the cord is biodegradable.

6. The stent of claim 5, wherein the polymeric material of the cord comprises Poly-L-Lactic Acid.

7. The stent of claim 6, wherein the Poly-L-Lactic Acid is impregnated with curcumin.

8. The stent of claim 1, wherein said at least single central lobe bounding cord members of said central lobes and said peripheral lobe bounding cord members of said peripheral lobes are elements of a continuous polymeric fiber cord that is biodegradable.

9. The stent of claim 8, wherein the polymeric fiber cord is impregnated with a therapeutic drug adapted to be released over time in a controlled manner into adjacent tissue when the stent is implanted in a host patient.

10. The stent of claim 8, wherein the polymeric fiber cord contains a radioactive agent that is adapted to provide localized radiation therapy at an implant site within a host patient.

11. The stent of claim 1, wherein the peripheral lobes are disposed exterior to the central lobes in the furled small-diameter state.

12. The stent of claim 1, wherein the peripheral lobes are confined within the central lobes in the furled small-diameter state.

13. The stent of claim 2 wherein the fiber cord includes a porous exterior coating that is impregnated with a therapeutic agent.

14. A biodegradable stent, comprising:
   a cord defining a coil structure having a predetermined length having a plurality of coil loops;
   longitudinally disposed reinforcing rods spaced around the coil structure and attached at selected points along the length of the coil structure at select ones of the loops;
   the coil structure and reinforcing rods comprising biodegradable polymeric material;
   the stent having a furled state and an expanded state, the effective diameter of the stent being significantly larger in the expanded state than in the furled state;
   the coil structure including a plurality of axially-aligned, successive central lobes that expand in size when the stent is converted from the furled state to the expanded state and each of the central lobes bounded by a portion of the cord;
   the coil structure including a plurality of peripheral lobes that exist in the furled state and merge into the central lobes in the expanded state, each central lobe having the same number of corresponding peripheral lobes associated therewith in the furled state, and each of said peripheral lobe bounded by a portion of the cord such that, for each central portion, the portion of the cord bounding each central portion and the associated portions of the cord bounding the associated peripheral portions comprise the associated one of the coil loops in the furled state; and
   wherein the cord is continuous from end-to-end along the coiled structure of the stent with successive portions of the cord defining the central lobes and the peripheral lobes corresponding to each central lobe in the furled state.

15. The biodegradable stent of claim 14 wherein the cord generally defines a helix in the expanded state.

16. A method of delivering a non-metallic stent to a vessel lumen of a host, comprising:
   providing a continuous cord of non-metallic material;
   winding the cord to define an elongated stent having multiple successive coils, each coil having a central lobe and a plurality of peripheral lobes;

attaching longitudinal support elements to the stent at circumferentially spaced intervals, the longitudinal support elements extending along the length of the stent and attached so as to space and support the coils;
inserting a balloon into the stent;
passing the stent through body vessels of the host to an implant site;
expanding the balloon to expand the stent by merging the peripheral lobes into the central lobes to add circumferential length to the central lobes, thus increasing the diameter of the stent;
collapsing the balloon; and
withdrawing the balloon to leave the stent in place at the implant site.

17. The method of claim 16 wherein the stent is at room temperature at the initiation of the step of passing the stent into the host body vessels and then rises to the body temperature of the host solely from the thermal energy of the host.

18. The method of claim 16 wherein the non-metallic material that is provided in the providing step is a biodegradable polymeric material.

19. The method of claim 16 further comprising delivering a therapeutic agent to host tissue adjacent to the stent from agents impregnated in the stent in a time controlled manner.

* * * * *